United States Patent [19]
Riihimaki et al.

[11] Patent Number: 5,294,413
[45] Date of Patent: * Mar. 15, 1994

[54] STERILIZATION AND STORAGE CASSETTE

[75] Inventors: Roy E. Riihimaki, Libertyville; James M. Kudla, Mt. Prospect, both of Ill.

[73] Assignee: Hu-Friedy Mfg. Co., Inc., Chicago, Ill.

[ * ] Notice: The portion of the term of this patent subsequent to Jun. 1, 2010 has been disclaimed.

[21] Appl. No.: 996,722

[22] Filed: Dec. 24, 1992

Related U.S. Application Data

[63] Continuation-in-part of Ser. No. 731,422, Jul. 17, 1991, Pat. No. 5,215,726.

[51] Int. Cl.⁵ ............................................. A61L 2/06
[52] U.S. Cl. ................................. 422/297; 422/300; 206/263; 206/363; 206/369; 206/370; 206/438; 206/565
[58] Field of Search ............... 422/297, 300, 310, 104; 206/210, 263, 363, 369, 370, 438, 480, 483, 565, 63.5; 220/324

[56] References Cited

U.S. PATENT DOCUMENTS

| | | | |
|---|---|---|---|
| D. 295,075 | 4/1988 | Jerge et al. | D24/9 |
| 1,157,733 | 10/1915 | Stevenson . | |
| 1,471,050 | 10/1923 | Montag . | |
| 2,147,510 | 2/1939 | Amick | 206/263 |
| 3,285,409 | 11/1966 | Loran | 206/564 X |
| 3,330,434 | 7/1967 | Bromley | 220/4 |
| 3,890,096 | 6/1975 | Nichol et al. | 21/105 |
| 4,046,254 | 9/1977 | Kramer | 206/370 |
| 4,135,868 | 1/1979 | Schainholz | 422/310 |
| 4,327,060 | 4/1982 | Nisii | 422/300 |
| 4,333,567 | 6/1982 | Leonard | 206/368 |
| 4,541,992 | 9/1985 | Jerge et al. | 422/300 |
| 4,577,755 | 3/1986 | Ramsay | 206/370 |
| 4,854,475 | 8/1989 | Riihimaki et al. | 220/337 |
| 4,865,821 | 9/1989 | Langdon | 422/300 |
| 4,959,199 | 9/1990 | Brewer | 422/300 |
| 4,978,510 | 12/1990 | Smith | 422/310 |
| 5,084,251 | 1/1992 | Thomas | 422/300 |
| 5,098,676 | 3/1992 | Brooks, Jr. | 422/292 |
| 5,127,537 | 7/1992 | Graham | 220/339 |

OTHER PUBLICATIONS

Svenska Dental Instruments AB, Vasby, Sweden, Applicants' Reference ("AR").
Syntex Dental Products, Bay Minette, Ala., Mar. 1982, applicants' Reference ("AS").
A-dec Trays & Tubs, Newberg, Oreg., Applicants' Reference ("AT").
Medin Corporation, Instrument Tray For Microsurgery, Applicants' Reference ("AAR").
Aesculap, Tuttlingen, West Germany, Applicants' Reference ("AAS").
Winston-Salem Dental Care Plan, Inc., Winston-Salem, N. C., Applicants' Reference ("AAT").

*Primary Examiner*—James C. Housel
*Assistant Examiner*—Milton I. Cano
*Attorney, Agent, or Firm*—Dressler, Goldsmith, Shore & Milnamow

[57] ABSTRACT

A sterilization and storage cassette formed of heat-resistant plastic and having two identical tray halves. In one embodiment, at least one tray half includes a rotatable retaining member for retaining dental instruments within the tray. In a second embodiment, a clamping member is inserted in one tray and at least one and preferably a plurality of instrument supports is inserted into the other tray. When the trays are closed together, the clamping member presses down upon and retains dental instruments placed on the supports. The trays are detachably connected through a hinge mechanism. Each tray has separate, distinct hinge members on one of its sides, and a set of separate, distinct latch members on another of its sides.

19 Claims, 8 Drawing Sheets

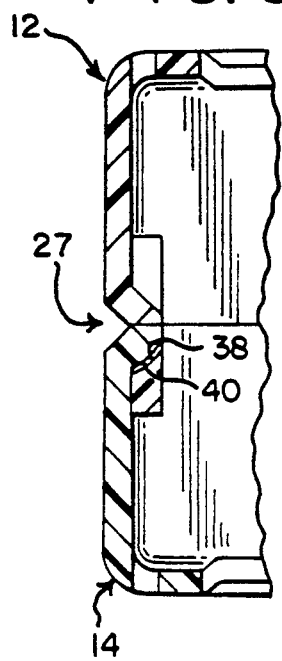
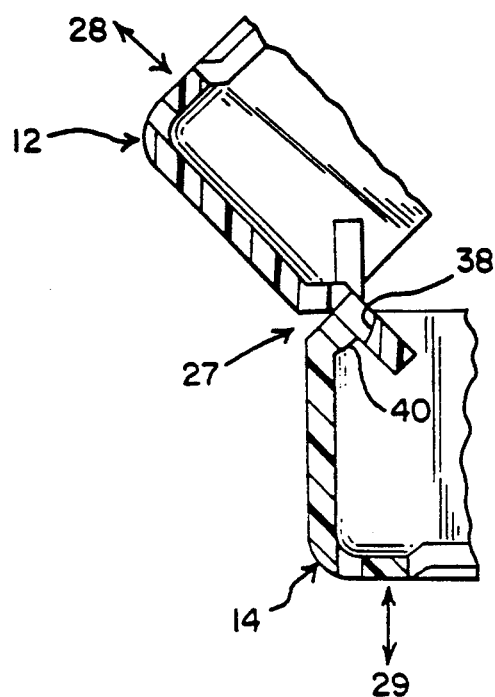
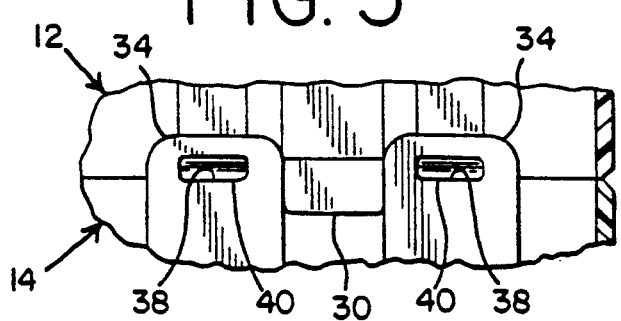

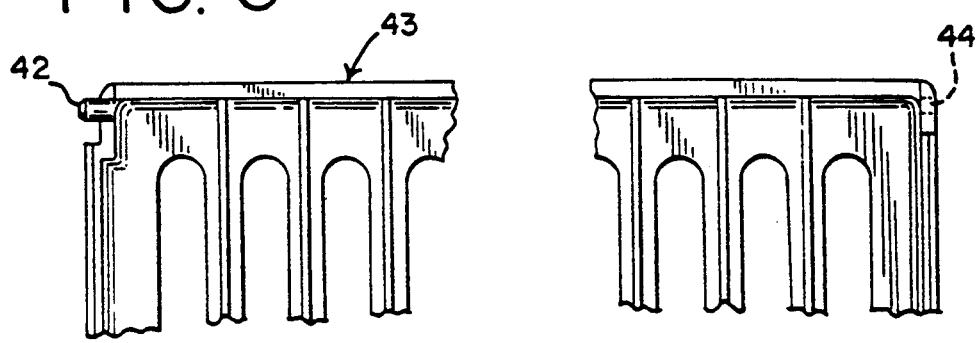
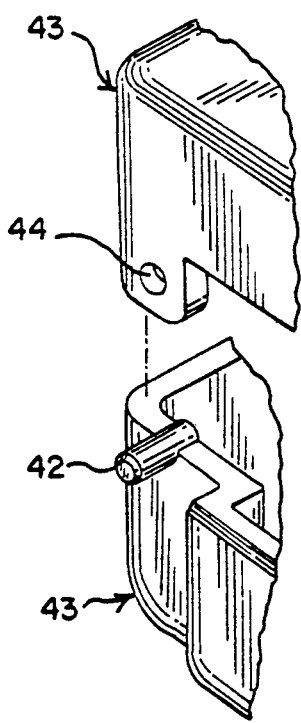
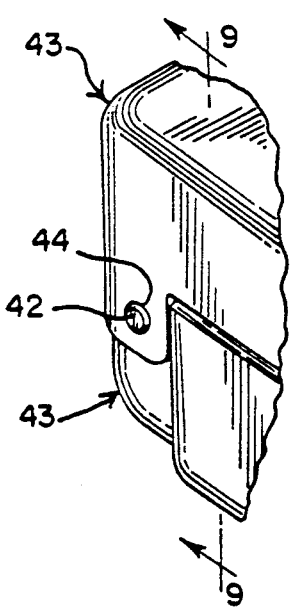
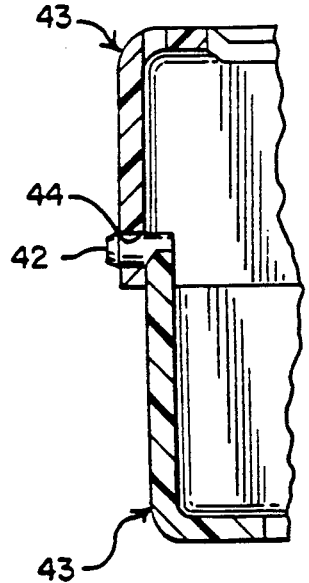

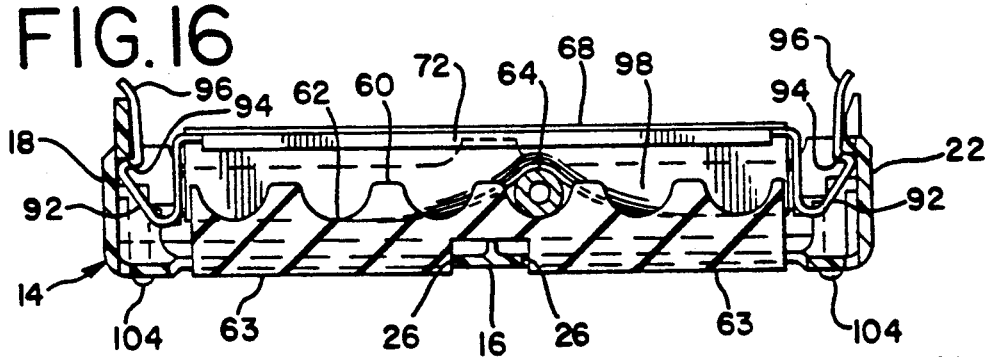
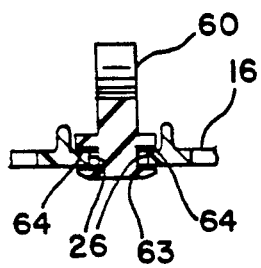
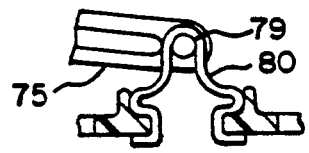
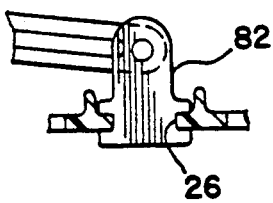
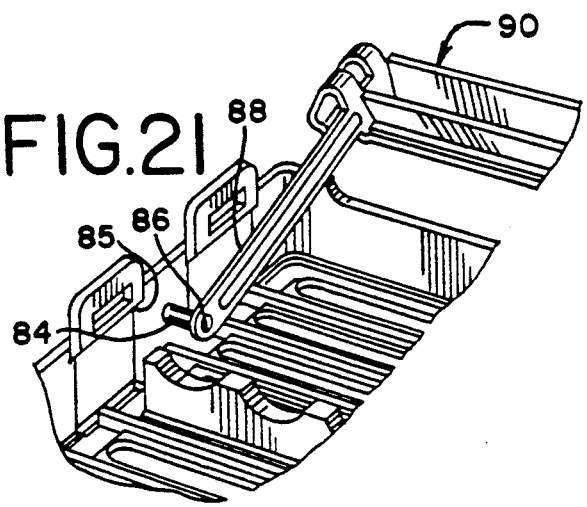

STERILIZATION AND STORAGE CASSETTE

CROSS-REFERENCES TO RELATED APPLICATIONS

This is a continuation-in-part of U.S. Pat. application Ser. No. 07/731,422, now U.S. Pat. No. 5,215,726.

BACKGROUND OF THE INVENTION

1) Field of the Invention

The present invention relates to an apparatus for sterilizing and storing medical/dental instruments, and in particular an improved instrument sterilization and storage cassette.

2) Description of the Related Art

The use of a cassette for the sterilization and storage of medical and dental instruments is well known. The instruments are held within the cassette in spaced relation to each other and the walls of the cassette. The means for holding the instruments within the cassette includes a variety of instrument supports, clamping members, and other instrument retaining means. The cassette is usually constructed from sheet metal. The cassette may include two tray halves which are detachably hinged together and can be latched together. See, for example, U.S. Pat. Nos. 4,541,992 and 4,854,475.

Notwithstanding advances made in the prior art, the manufacture of instrument sterilization and storage cassettes from sheet metal has remained costly, particularly in higher volumes. Also, sheet metal designs have remained relatively cumbersome.

Making such cassettes from plastic has advantages. Plastic is lightweight. The cost of manufacture of a cassette formed of plastic can be less than that of sheet metal, particularly when produced in higher volumes.

Further, making such cassettes from two substantially identical halves has advantages. The cost of tooling for manufacture, as well as the costs of inventory and assembly, is substantially reduced when the cassette can be constructed from two substantially identical halves.

It would be desirable to construct an instrument sterilization and storage cassette from a heat-resistant plastic, wherein each half of the cassette is substantially identical, and includes separate hinge and latch elements for convenient use.

Further, it would be desirable to combine the design advantages of constructing a cassette having two identical, interchangeable halves and being manufactured from a heat-resistant plastic with the design features of the instrument sterilization and storage cassette disclosed in parent application Ser. No. 07/731,422, which is incorporated by reference herein.

SUMMARY OF THE INVENTION

The instrument sterilization and storage cassette according to the present invention has two substantially identical trays, each constructed from heat-resistant plastic. Each tray is designed such that it can be fitted together with another tray of the same design to form a cassette. The resulting cassette can store either one or two tiers of instruments.

The trays are detachably hinged together. Latch members secure the trays in a closed position.

The hinge and latch are separate elements. The hinge has two separate, distinct members located on the same side of each tray. The latch has two separate, distinct members located on a different side of the tray.

In one embodiment in accordance with the invention, at least one and preferably a plurality of instrument supports is located within at least one tray. A rotatable retaining member is located within the same tray. The retaining member moves between an open position and an instrument-retaining position. In the instrument-retaining position, the retaining member exerts pressure on dental instruments that are placed on the instrument supports so as to retain the instruments at their locations on the supports Preferably, there is a detent which biases the retaining member in the instrument-retaining position.

In an alternative embodiment in accordance with the invention, at least one and preferably a plurality of instrument supports is located on one tray and a retaining member is located on the other tray. When the trays are closed together, the retaining member exerts pressure on dental instruments that are placed on the supports so as to retain the instruments at their locations on the supports.

These and other aspects and attributes of the present invention will be discussed with reference to the following drawings and accompanying specification.

BRIEF DESCRIPTION OF THE DRAWINGS

FIG. 3 is a cross-sectional view taken along the plane 3—3 in FIG. 1;

FIG. 4 is a cross-sectional view similar to the cross-sectional view shown in FIG. 3 wherein the trays are in a partially open position;

FIG. 5 is a cross-sectional view taken along the plane 5—5 in FIG. 1;

FIG. 6 is a partial view of hinge members of an alternative embodiment of a tray in accordance with the invention;

FIG. 7 is a partial perspective view of the hinge members of two adjacent trays of the alternative embodiment shown in FIG. 6;

FIG. 8 is a partial perspective view of the trays shown in FIG. 7 wherein the two trays are hinged together;

FIG. 9 is a cross-sectional view taken along the plane 9—9 in FIG. 8;

FIG. 16 is a cross-sectional view taken along the plane 16—16 in FIG. 14;

FIG. 17 is a cross-sectional view taken along the plane 17—17 in FIG. 14;

FIG. 18 is a partial perspective view of the retaining member at its connection to the tray as shown in FIG. 2;

FIG. 19 is a partial cross-sectional view of an alternative embodiment of a retainer clip with a hinge pin of an arm of a rotatable retaining member inserted therein;

FIG. 20 is a partial, cross-sectional view of a second alternative embodiment of a retainer clip with a hinge pin of an arm of a rotatable retaining member inserted therein;

FIG. 21 is a partial perspective view of an alternative embodiment of the connection between the rotatable retaining member and the side wall of the tray.

DETAILED DESCRIPTION OF THE INVENTION

The following is a detailed description of the invention. The detailed description is not intended to be an exhaustive description of all embodiments within the scope of the invention and is not intended to limit the scope of the claims to the disclosed embodiments. Other embodiments within the scope of the claims will be apparent to those skilled in the art.

Figure 1:
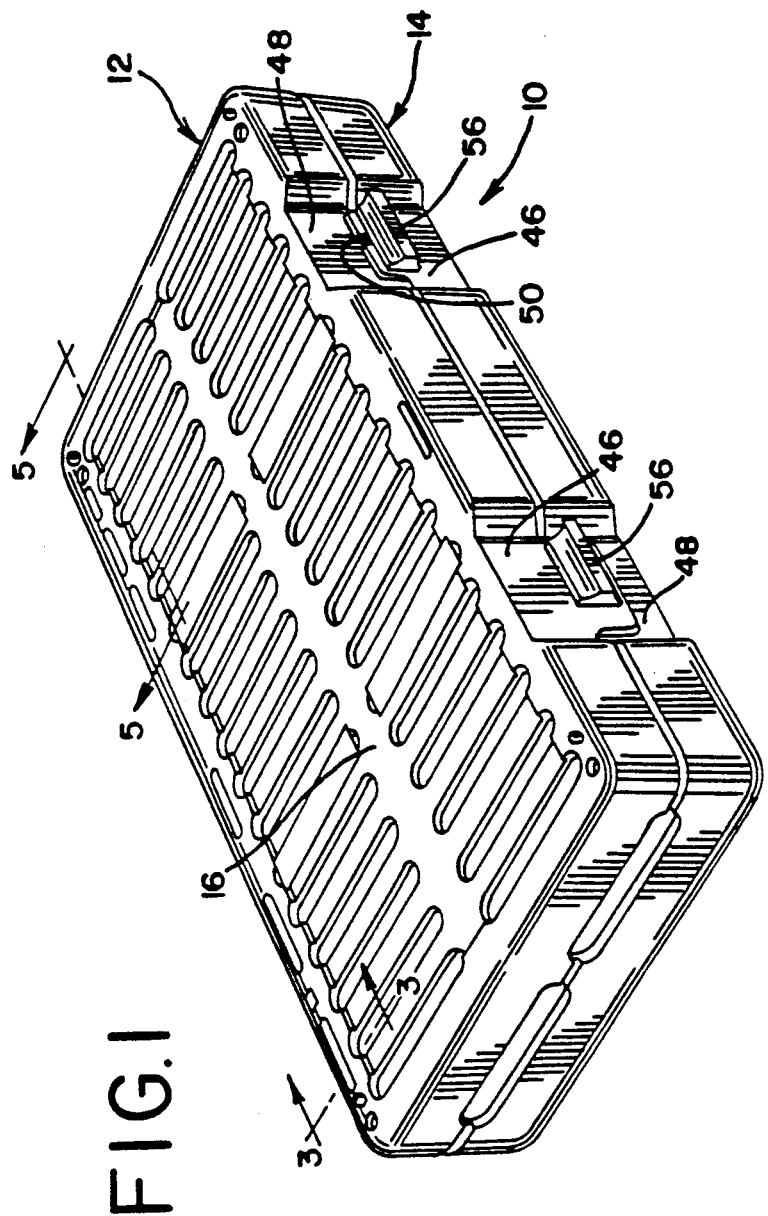
FIG. 1 is a perspective view of a cassette in with the invention wherein the trays are in a closed position.
Figure 2:
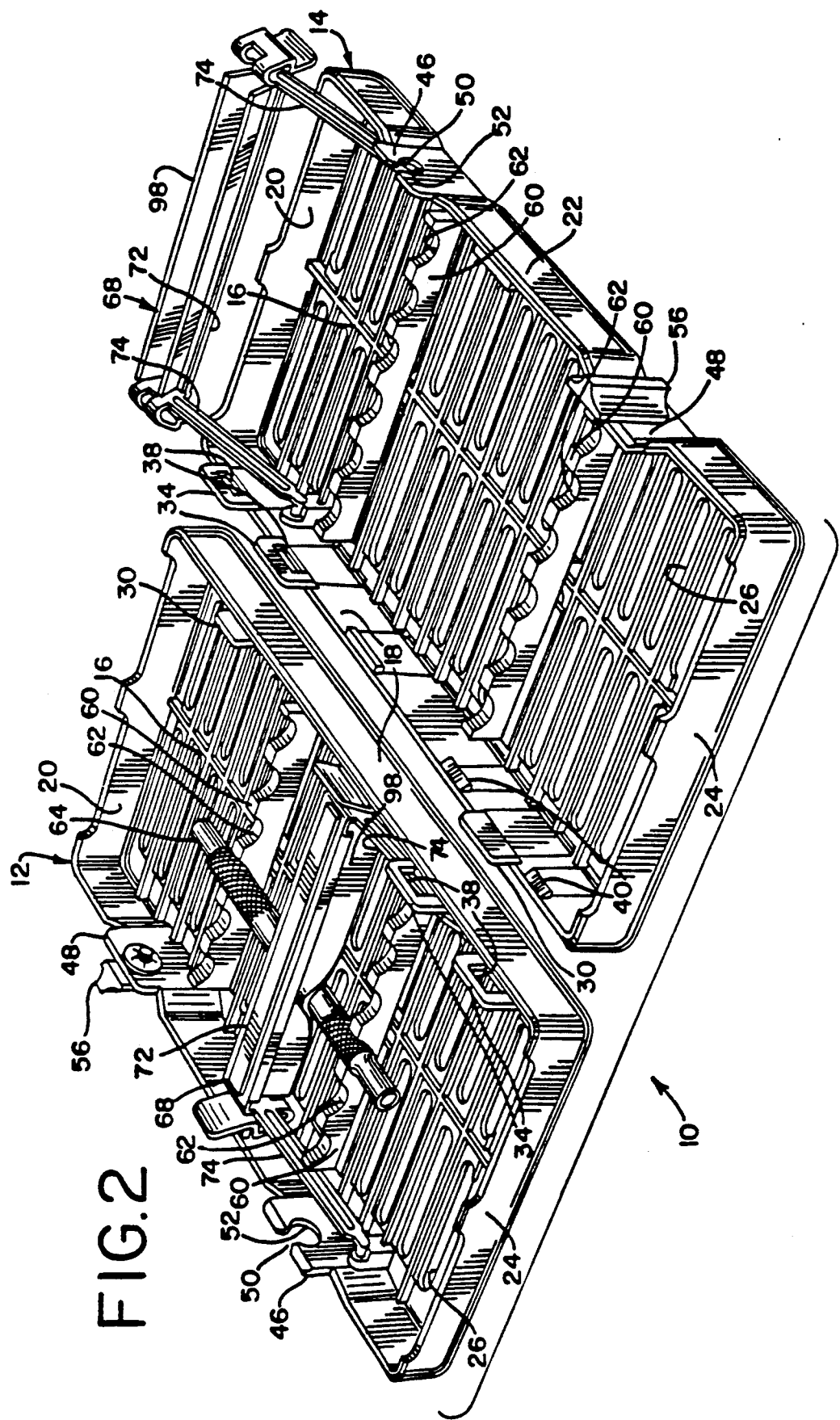
FIG. 2 is a perspective view of a first embodiment of the cassette in accordance with the invention wherein the trays are in an open position.

Referring to FIGS. 1 and 2, there is shown a first embodiment of the sterilization and storage cassette in accordance with the invention. The cassette 10 includes two trays which will be designated herein as a first tray 12 and a second tray 14 for the purposes of illustration. The first and second trays are latched in a closed position in FIG. 1 so as to form a box-like cassette which contains dental instruments therein. The interior of the cassette is a bounded sterilization region wherein medical and dental instruments may be sterilized with conventional techniques.

In FIG. 2, the trays 12 and 14 are shown opened and separated. Each tray is identically configured, according to the design described below.

Each tray includes a substantially planar face or panel 16 and four sidewalls 18, 20, 22 and 24 extending upwardly from the panels. The panels have a plurality of openings 26 for permitting the free flow of air or sterilization fluids into the cassette.

A hinge mechanism detachably connects the first tray 12 and second tray 14 together. The hinge mechanism includes two distinct, separate hinge portions located on the same side 18 of each tray 12 and 14. The first hinge portion is a single tab or finger 30 extending upwardly from the side of the tray. The second hinge portion is a set of dual tabs or fingers 34 extending upwardly from a different location on the same side of the tray.

The movement of the hinge mechanism 27 is shown in FIGS. 3 and 4. The trays 12 and 14 are movable from a closed position (FIG. 3) to a partially opened position (FIG. 4). When in the partially opened position, the trays may be engaged and disengaged by moving them in the direction of the arrows 28 and 29.

The fingers of the first and second hinge portions are located such that when two trays are brought together, the single finger 30 on the first tray 12 will slide between the dual fingers 34 on the second tray 14 in an interlocking arrangement. As shown in FIG. 5, the single finger 30 on the first tray 12 fits between the dual fingers 34 on the second tray 14. Similarly, the single finger 30 on the second tray 14 fits between the dual fingers 34 on the first tray 12 (not illustrated).

Each of the dual fingers 34 on each tray defines apertures 38 that permit insertion of protrusions 40 that extend from the side walls 18 of the other tray. When the trays are in a closed position as shown in FIGS. 3 and 5, the protrusions 40 fit snugly within the apertures 38 and prevent the trays 12 and 14 from separating. When the trays are opened in a rotating manner into an open position as shown in FIG. 4, the protrusions 40 are withdrawn from the apertures 38, thus permitting disengagement and separation of the trays.

An alternative hinge construction is shown in FIGS. 6–9. The alternative construction includes a hinge pintle 42 on one end of each tray 43 and an opening 44 on the other end of the tray as shown in FIG. 6. When two trays are brought adjacent to each other (FIG. 7) and then fitted together (FIGS. 8 and 9), the hinge pintles 42 fit within the hinge openings 44 in order to form a hinge connection between the trays.

Referring back to FIG. 2, there are two distinct, separate latch portions 46 and 48 on the same side 22 of each tray which are located on the side 22 opposite the side 18 containing the hinge portions. The first latch portion 46 is a slotted receiving member or tab extending upwardly from the side 22 of each tray. The tab has a slot 50 with a narrow opening which leads to a wider, circular portion 52. The second latch portion 48 is a tab with a rotatable key 56 that is at a different location on the same side 22 of the tray.

As seen in FIG. 1, the first and second latch portions 46 and 48 on each tray are located such that when two trays are brought together, the first and second latch portions of the opposing trays are adjacent to each other and the rotatable key 56 on each tray can be inserted into the slot of the other tray. Thus the opposing latch portions on opposing trays are slidably engageable with each other.

Figure 10:
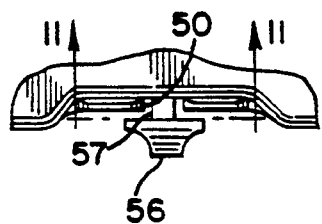
FIG. 10 is a partial top plan view of a closed cassette showing the latch portions wherein the key is in the unlatched position.
Figure 11:
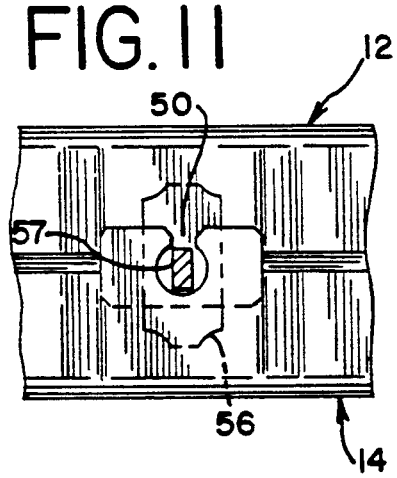
FIG. 11 is a cross-sectional view taken along the plane 11—11 in FIG. 10 with the key handle being shown with phantom lines.

Referring to FIGS. 10 and 11, the width of the stem 57 of the key 56 is less than the width of the slot 50. Thus, when the key 56 is oriented so that its width extends across the width of the slot 50, then the key may be inserted into and removed from the slot.

Figure 12:
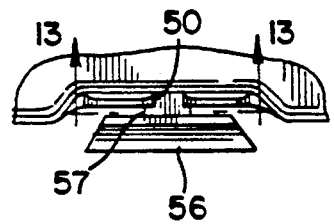
FIG. 12 is a partial top plan view of a closed cassette showing the latch portions wherein the key is rotated into a latched position.
Figure 13:
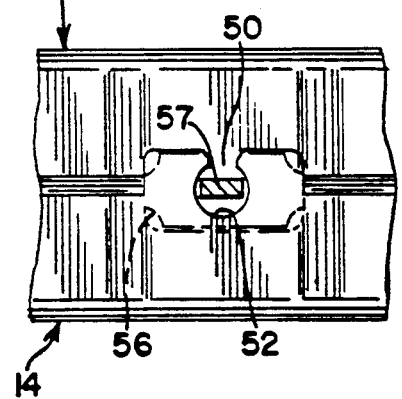
FIG. 13 is a cross-sectional view taken along the plane 13—13 in FIG. 12 with the key handle being shown with phantom lines.

Conversely, referring to FIGS. 12 and 13, the length of the stem 57 of the key 56 is greater than the width of slot 50, but less than the diameter of the circular portion 52 of the slot. When the key is rotated so that its length extends across the width of the slot, the key cannot be removed from the slot and the trays 12 and 14 are latched together.

The trays as described herein, including the hinge and latch portions, are formed of a heat resistant material, preferably a heat resistant plastic such as polysulfone. Since each tray is substantially identical, the trays may be formed from the same mold.

Referring to FIG. 2, at least one and preferably a plurality of removable instrument supports 60 is inserted into at least one and preferably both trays 12 and 14 of the cassette 10. The instrument supports have multiple U-shaped recesses 62 in order to separately hold instruments 64 placed thereon. The supports 60 are upstanding from the interior surface of the panel 16 so as to separate the instruments from the panel. Thus, instruments placed on the supports are kept in spaced relation to each other and the tray panel.

Figure 14:
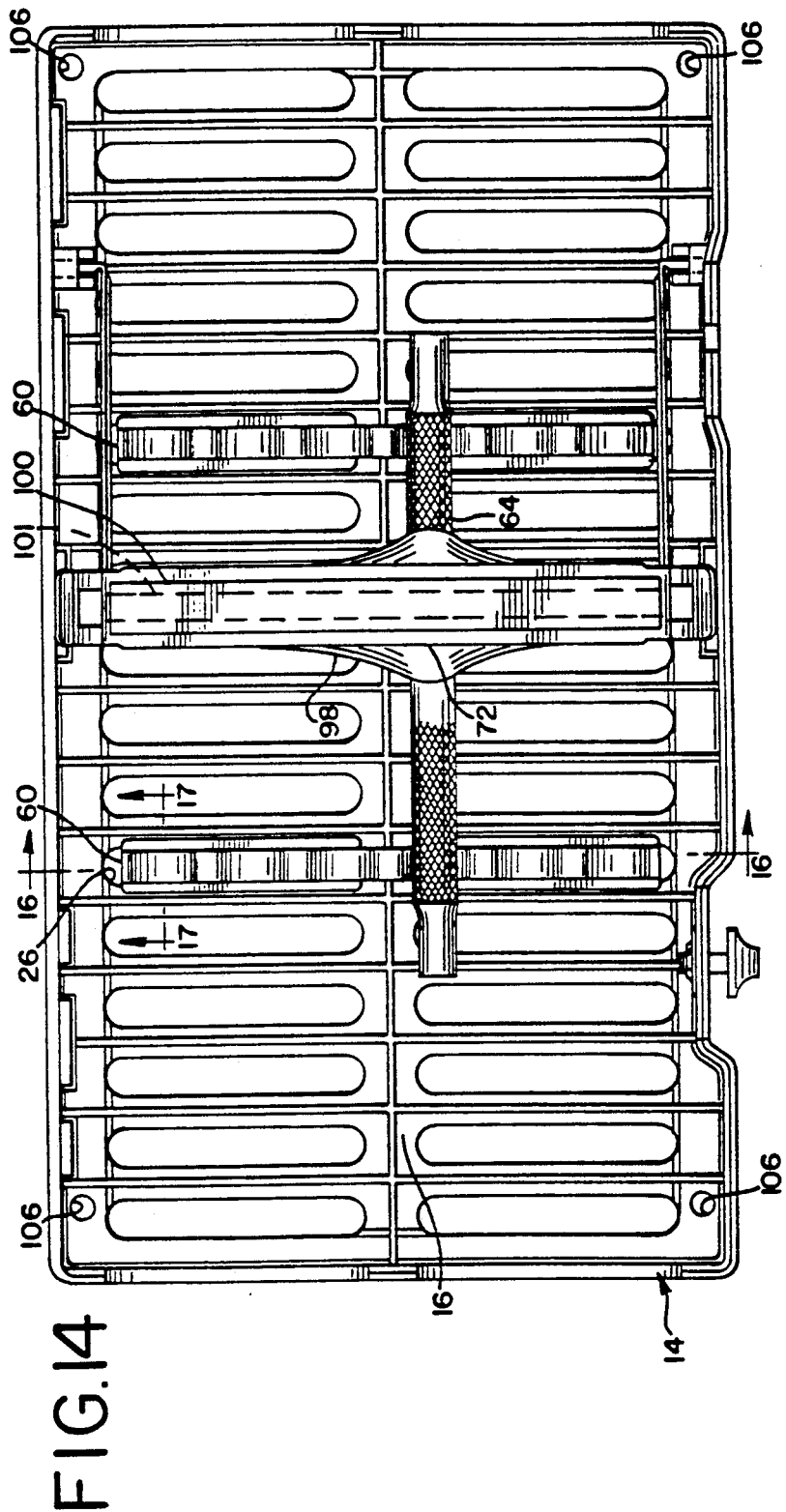
FIG. 14 is a top plan view of the first embodiment of one tray of the cassette in accordance with the invention wherein a dental instrument is inserted therein.
Figure 15:
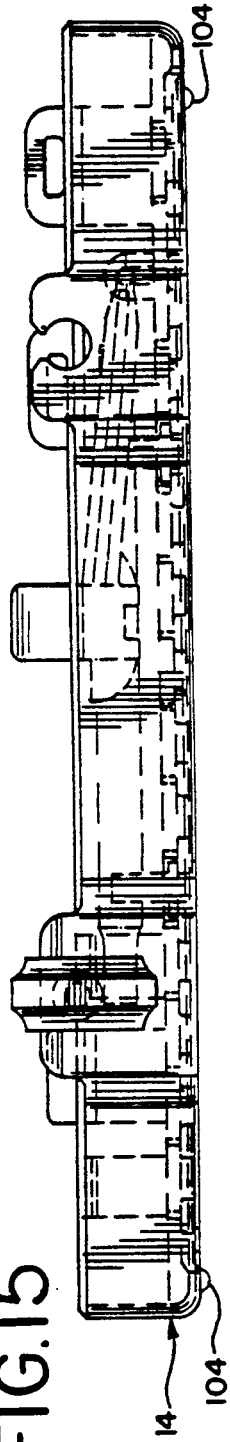
FIG. 15 is a side elevational view of the tray shown in FIG. 14.

Referring to FIGS. 14, 16 and 17, each instrument support 60 is attached to the interior of a tray 14 by inserting its bottom portion 63 (FIGS. 16 and 17) through an opening 26 in a panel 16. Referring to FIG. 17, the bottom portion 63 has grooves 64 into which the edges of the opening 26 in the panel 16 are fitted in order to secure the instrument support within the opening.

Preferably, each instrument support is formed of heat-resistant silicon rubber so as to provide a soft, resilient surface for placement of instruments. In the construction disclosed herein, the resiliency of the supports 60 permits them to be inserted and removed from the openings 26 in the trays 12 and 14. Thus, the supports are detachably connected to the trays and may be attached at various locations within the trays.

Rotatable retaining members 68 are located within one and preferably both of the trays of the cassette 10 as shown in FIG. 2. Also, each rotatable retaining member includes a crossbar 72 with two arms 74 extending perpendicularly from the ends of the crossbar. Referring to a partial view of the rotatable retaining member in FIG. 18, the free end of each arm 74 has a hinge pin 78 that is inserted into an opening in the side wall 18 of the tray.

Each rotatable retaining member 68 rotates about its hinge pins 78 between an open position wherein the crossbar 72 is spaced away from the panel of its respective tray and a closed position wherein the crossbar is adjacent to the face of the panel. In FIG. 2, retaining member 68 in tray 12 is in a closed position and retaining member 68 in tray 14 is in an open position.

Alternative embodiments of the connection between the rotatable retaining member 68 and the tray are shown in FIGS. 19-21. In FIG. 19, a hinge pin 79 extends from the arm 75 of the rotatable retaining member and is held by a hinge clip 80. The hinge clip may be made a spring steel or plastic piece that is inserted into an opening in the panel of a tray.

Alternatively, referring to FIG. 20, the hinge clip 82 may be formed of heat-resistant silicon rubber that is insertable into an opening 26 in the panel of a tray.

Alternatively, referring to FIG. 21, a hinge pin 84 may extend inwardly from an upstanding wall 85 of a tray and be inserted into an opening 86 in an arm 88 of a rotatable retaining member 90.

Referring to FIG. 16, the rotatable retaining member 68 has retaining clips 92 on each side. There are corresponding ledges or detents 94 extending inwardly from the side walls 18 and 22 of the tray 14 for engagement of the retaining clips in order to retain the retaining member in the closed position Each retaining clip has an upstanding leaves 96 for gripping and squeezing inwardly to release the clip from the detent.

The rotatable retaining member 68, including its crossbar 72, arms 74 and retaining clips 92, is formed of rigid heat resistant material, preferably a material which permits a small amount of elastic bending such as stainless steel. Such bending permits the arms 74 to deflect slightly in order to permit insertion and removal of the hinge pins 78 into the openings in the side walls 18 and 22 of the trays. Thus, the rotatable retaining members 68 are detachably connected to the trays 12 and 14.

A clamping member 98 is connected to the crossbar 72 of the rotatable retaining member 68 as seen in FIGS. 2, 14, 15, 16 and 18. Referring to FIG. 14, the clamping member 98 has a top portion 100 that is inserted into an opening 101 in the crossbar. The top portion is grooved to permit insertion of the edges of the opening in the crossbar in order to secure the clamping member to the crossbar.

Referring to FIG. 16, the clamping member 98 extends downwardly from the crossbar 72 toward panel 16 of the tray 14 when the retaining member 68 is in the closed position. When an instrument 64 is placed on the instrument support 60 and the retaining member 68 is rotated into a closed position against the instrument, the resilient clamping member 98 deflects and compresses in order to grip the instrument firmly.

Preferably, the clamping member 98 is formed of heat-resistant silicon rubber. The clamping member 98 is sufficiently resilient to permit its insertion into and removal from the opening in the crossbar 72. Thus, the clamping member is detachably connected to the crossbar Referring to FIGS. 15 and 16, stacking feet 104 extend outwardly from the panel 16 of each tray. Stacking holes 106 are defined in each panel as shown in FIG. 14. The stacking feet 104 and stacking holes 106 are located so as to match each other when closed cassettes 10 are stacked on each other. The stacking feet of one cassette insert into the stacking holes of a neighboring cassette so as to restrict sliding motion of the cassettes and maintain the stability of a stack of cassettes.

In the operation and use of the first embodiment of the cassette 10 in accordance with the invention as shown in FIG. 2, the cassette permits the loading of a multiplicity of medical or dental instruments 64 on one or both trays of the cassette. After such loading and closure of the rotatable retaining members 68, the trays 12 and 14 can be closed together and latched. Thus, the closed cassette 10 holds one or preferably two levels or tiers of instruments for sterilization or storage.

Figure 22:
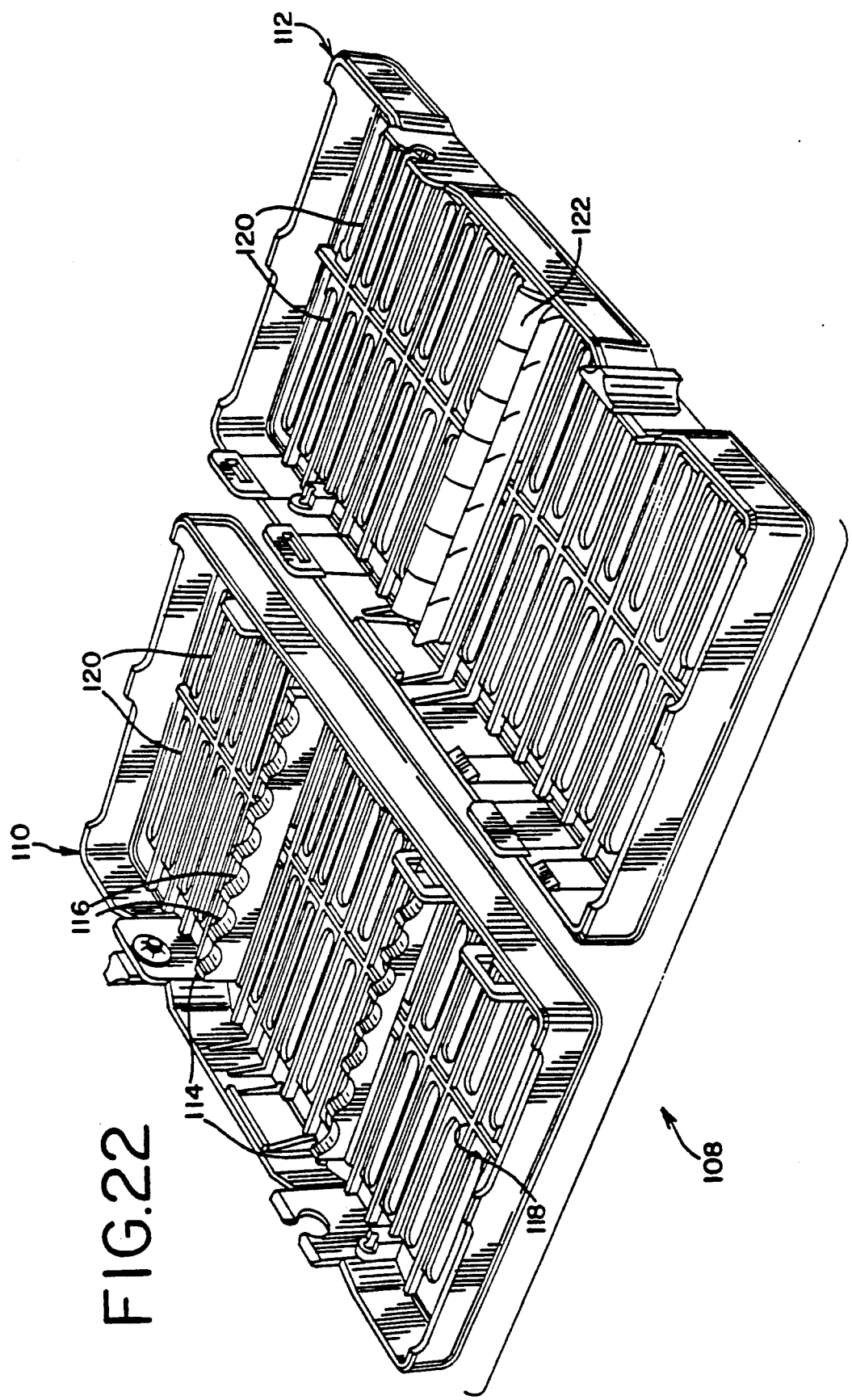
FIG. 22 is a perspective view of a second embodiment of a cassette in accordance with the invention.

An alternative embodiment of the cassette 108 in accordance with the invention is shown in FIG. 22. The design and construction of its trays 110 and 112 are identical to that of the first embodiment. At least one and preferably a plurality of instrument supports 114 is inserted onto one tray 110. The supports 114 have multiple u-shaped recesses 116 in order to separately hold instruments placed thereon. The supports 114 are upstanding from the interior surface of the panel 118 so as to separate the instruments from the panel. Thus, instruments placed on the supports are kept in spaced relation to each other and the panel.

Each support 114 is attached to the panel 118 by inserting its bottom portion through an opening 120 in the face of the tray. The bottom portion has a groove into which the edges of the opening in the tray are fitted in order to secure the support within the opening similar to the construction of the instrument support 60 shown in FIG. 17.

Preferably, each instrument support 114 is formed of heat resistant silicone rubber so as to provide a soft, resilient surface for placement of instruments, and to permit them to be inserted and removed from the openings 120 in the tray 110. Thus, the supports 114 are detachably connected to a tray and may be attached at various locations within a tray.

A clamping member 122 is removably inserted into the openings 120 in the other tray 112 of the second embodiment 108 as shown in FIG. 22. When the two trays 110 and 112 are closed together, the clamping member 122 presses against instruments placed on the instrument supports 114 and thus retains them within the U-shaped recesses 116 in the supports.

As in the first embodiment, the trays 110 and 112 in the second embodiment 108, including their hinge and latch structure, are substantially identical to each other.

The hinge and latch portions are configured to match with each other when two trays are brought together in the manner discussed above relating to the first embodiment.

In the operation and use of the second embodiment, in accordance with the invention, the cassette 108 permits the loading of a multiplicity of medical or dental instruments on one tray 110. After such loading, the trays 110 and 112 are closed together and latched. Thus, the closed cassette 108 holds a single-tier of instruments for sterilization and storage.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. An instrument sterilization and storage cassette comprising:
   first and second substantially identical, trays, each of said trays being formed of heat resistant plastic, each of said trays defining a plurality of sterilization openings, wherein said trays are connectable to each other to form a bounded sterilization region; least one of said trays; and
   a rotatable retaining member located within said at least one tray, said retaining member being rotatably connected to opposite said sides of tray so as to be rotatable about an axis of rotation between an open position and an instrument retaining position.

2. An instrument sterilization and storage cassette in accordance with claim 1 wherein each of said trays contains one of said retaining members and at least one of said instrument supports.

3. An instrument sterilization and storage cassette in accordance with claim 1 wherein each of said trays includes a plurality of said instrument supports.

4. An instrument sterilization and storage cassette in accordance with claim 1 wherein said retaining member is formed in part of steel.

5. An instrument sterilization and storage cassette in accordance with claim 1 wherein each of said trays includes a detent for holding said retaining member in said instrument retaining position.

6. An instrument sterilization and storage cassette in accordance with claim 1 wherein said retaining member includes a clamping member.

7. An instrument sterilization and storage cassette in accordance with claim 1 including a latch mechanism on said cassette for latching said trays together.

8. An instrument sterilization and storage cassette in accordance with claim 7 wherein said latch mechanism includes a slotted receiving member and a rotatable key member that is insertable into said slotted receiving member.

9. An instrument sterilization and storage cassette in accordance with claim 8 wherein each of said trays includes one of said slotted receiving members and one of said rotatable key members.

10. An instrument sterilization and storage cassette in accordance with claim 1 including a hinge connection between said first and second trays.

11. An instrument sterilization and storage cassette in accordance with claim 10 wherein said hinge connection includes an aperture defined on one of said trays and a hinge pintle extending from the other of said trays for insertion into said aperture.

12. A cassette as in claim 1 wherein said instrument support has first and second ends and wherein said retaining member is attached to said selected tray at first and second pivot points with each said pivot point located adjacent to a respective one of said ends.

13. A cassette as in claim 1 wherein said retaining member includes an instrument retaining bar spaced from said axis of rotation.

14. An instrument sterilization and storage cassette comprising:
   first and second molded, plastic, sterilizable, substantially identical trays wherein said trays may be coupled together and wherein at least one of said trays carries a rotatably mounted retaining member coupled to said one tray at first and second spaced apart pivot points which define an axis of rotation and wherein said retaining member includes an instrument retaining bar spaced from said axis of rotation.

15. A cassette as in claim 14 wherein said one tray carries an elongated instrument support member having first and second ends wherein each of said pivot points is located adjacent to a respective one of said ends.

16. A cassette as in claim 14 wherein at least a portion of said instrument retaining bar is deflectable.

17. A cassette formed of two substantially identical elements wherein each element comprises:
   a molded, sterilizable tray having spaced apart bounding sides joined by a closing panel;
   first and second complimentary hinge members carried on a selected one of said sides, wherein said first and second hinge members are spaced apart from each other;
   a latch member carried on another side wherein said tray can be rotatably coupled to a second substantially identical tray by said complimentary hinge elements and latched thereto by said latch member; and
   a retaining member movably mountable on said tray at first and second spaced apart regions wherein each of said regions is adjacent to a respective opposite one of said bounding sides.

18. A cassette as in claim 17 wherein said retaining member includes a deformable resilient instrument retaining portion.

19. A cassette as in claim 17 wherein said retaining member is rotatably movable relative to said tray.

* * * * *